(12) United States Patent
Aberg

(10) Patent No.: US 6,432,446 B2
(45) Date of Patent: *Aug. 13, 2002

(54) NON-ARRHYTHMOGENIC METABOLITE OF OXYBUTYNIN

(75) Inventor: A. K. Gunnar Aberg, Sarasota, FL (US)

(73) Assignee: Bridge Pharma, Inc., Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/775,060

(22) Filed: Feb. 1, 2001

Related U.S. Application Data

(60) Provisional application No. 60/179,960, filed on Feb. 3, 2000.

(51) Int. Cl.$^7$ ............................ A61K 9/22; A61K 9/12; A61K 9/14; A61K 9/20; A61K 9/48
(52) U.S. Cl. ...................... 424/468; 424/436; 424/451; 424/449; 424/464; 424/489; 424/44; 424/45
(58) Field of Search ................................ 424/468, 436, 424/451, 449, 464, 489; 514/617, 964, 966, 962

(56) References Cited

U.S. PATENT DOCUMENTS

| | | | | |
|---|---|---|---|---|
| 3,536,809 | A | | 10/1970 | Applezweig .................. 424/28 |
| 3,598,123 | A | | 8/1971 | Zaffaroni ..................... 128/268 |
| 3,845,770 | A | | 11/1974 | Theeuwes et al. .......... 128/260 |
| 3,916,899 | A | | 11/1975 | Theeuwes et al. .......... 128/260 |
| 4,008,719 | A | | 2/1977 | Theeuwes et al. .......... 128/260 |
| 5,532,278 | A | | 7/1996 | Aberg et al. ................. 514/617 |
| 5,677,346 | A | * | 10/1997 | Aberg et al. ................. 424/449 |
| 6,123,961 | A | * | 9/2000 | Aberg ......................... 424/468 |

FOREIGN PATENT DOCUMENTS

| | | |
|---|---|---|
| WO | 92/20377 | 11/1992 |

OTHER PUBLICATIONS

Circulation vol. 80, No. 4, Oct. 1989 pp.1063–1069; Point of View; Levine, et al.; "Mechanisms and Risk Factors for Proarrhythmia with Type Ia Compared with Ic Antiarrhythmic Drug Therapy".*

The American Journal of Cardiology, vol. 50, Nov. 1982; pp. 1099–1103; Browne, et al.; "Influence of the Autonomic Nervous System on the Q–T Interval in Man".*

BMJ vol. 303, Aug. 31, 1991; pp. 519–520; AH Watt; "Terodiline and torsades de pointes".*

J.Pharmacology and Experimental Therapeutics, vol. 290, No. 3 pp. 1417–1426; Shuba, et al.; "Action Potentials, Contraction, and Membrane Currents in Guinea Pig Ventricular Preparations Treated with the Antispasmodic Agent Terodiline", 1999.*

BR. Heart J, 1995; 74: pp. 53–56; Thomas et al.; "Concentration dependent cardiotoxicity of terodiline in patients treated for urinary incontinence".*

Arzneim.–Forsch/Drug Res. 48 (II), 1012–1018 (1998); Smith et al.; "Comparison of the Antimuscarinic and Antispasmodic Actions of Racemic Oxybutynin and Desethyloxybutynin and their Enantiomers with Those of Racemic Terodiline".*

British Journal of Pharamacology (2000) 131, 245–254; Jones, et al.; "Differences in the effects of urinary incontinence agents S–oxybutynin and terodiline on cardiac K+ currents and action potentials".*

Journal of Cardiovascular Pharmacology 35: pp. 334–340; Jones, et al.; "Analysis of the Electrophysiologic Effects of Short–Term Oxybutynin on Guinea Pig and Rabbit Ventricular Cells", 2000.*

British Journal of Pharmacology; (1998) 125, 1138–1143; Jones et al.; "Inhibition of the rapid component of the delayed–rectifier K+ current by therapeutic concentrations of the antispasmodic agent terodiline".*

Xenobiotica, 1992, vol. 22, No. 7, 859–869; Hughes, et al.; "Measurement of oxybutynin and its N–desethyl metabolite in plasma, and its application to pharmacokinetic studies in young, elderly and frail elderly volunteers".*

British Journal of Clinical Pharmacology 41, 73–75; Hussain et al.; "Effect of oxybutynin on the Qtc interval in elderly patients with urinary incontinence", 1996.*

\* cited by examiner

*Primary Examiner*—Thurman K. Page
*Assistant Examiner*—Rachel M. Bennett
(74) *Attorney, Agent, or Firm*—Nields & Lemack

(57) ABSTRACT

A method of treating disorders involving the urethrogentical tract by administering to pateints in need therof therapeutically effective amounts of the desethyl metabolite of oxybutynin and/or the optically active isomers thereof, which are free from said cardiac side effect of oxybutynin, while maintaining the therapeutic activities of oxybutynin or the optically active isomers thereof.

7 Claims, No Drawings

NON-ARRHYTHMOGENIC METABOLITE OF OXYBUTYNIN

This application claims benefit of Ser. No. 60/179,960 filed Feb. 3, 2000.

FIELD OF THE INVENTION

The invention relates to the desmethyl metabolite of 4-diethylamino-2-butynyl cyclohexylphenylglycolate and optical isomers thereof. The compound 4-diethylamino-2-butynyl cyclohexylphenylglycolate has the generic name oxybutynin (OXY) and is an approved drug for the management of urinary incontinence. The drug may also be used in patients suffering from gastrointestinal hypermotility disorders.

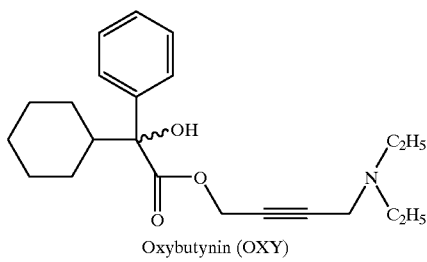

Oxybutynin (OXY)

The compound 4-ethylamino-2-butynyl cyclohexylphenylglycolate, also called desethyloxybutynin (DEO), and has the following chemical structure:

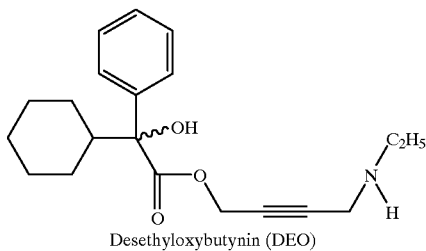

Desethyloxybutynin (DEO)

BACKGROUND OF THE INVENTION

Racemic oxybutynin (OXY) is used therapeutically in the treatment of urinary incontinence due to detrusor muscle instability. The drug may also be used in patients suffering from gastrointestinal hypermotility disorders such as for example irritable bowel syndrome (IBS). OXY exerts a spasmolytic effect by inhibiting the contractions of smooth muscle with cholinergic innervation.

In patients with conditions characterized by involuntary bladder contractions, clinical studies have demonstrated that OXY increases bladder capacity, diminishes the frequency of involuntary contractions of the detrusor muscle, and delays the initial desire to void. OXY is therefore useful in the treatment and prevention of both incontinence and frequent voluntary urination.

Racemic oxybutynin consists of a 50/50 mixture of R(−)-oxybutynin and S(+)-oxybutynin. It has been shown that practically all of the anticholinergic activity of OXY resides in the R(−)-isomer, while the activity of the S(+)-isomer is due to its direct spasmolytic activity (Aberg et al. U.S. Pat. No. 5,532,278.)

One clinically important metabolite of OXY has been identified in humans after administration of OXY and is called desethyloxybutynin (DEO) (Westlin, L., 1985. Internal report, Smith & Nephew Pharmaceuticals Ltd.). A second metabolite, didesethyloxybutynin (DIDEO) has been synthesized and found to have low pharmacological activity and short duration of action (Aberg et al. to be published.) A third metabolite, called N-oxide-oxybutynin, has been suggested but may not be chemically stable (Lindeke B. et al., 1981 Metabolism of Oxybutynin . . . Biomed Mass Spectrometry. 1981, 8:506–513).

SUMMARY OF THE INVENTION

The problems of the prior art have been overcome by the present invention, which is directed to a method of treating disorders involving the urethrogential tract by administering to pateints in need thereof therapeutically effective amounts of the desethyl metabolite of oxybutynin and/or the optically active isomers thereof, which are free from said cardiac side effect of oxybutynin, while maintaining the therapeutic activities of oxybutynin or the optically active isomers thereof.

It has now unexpectedly been found that oxybutynin causes a prolongation of the QTc-interval of the EKG. Such prolongation of the QTc-interval is known to be caused by inhibition of the delayed rectifier potassium current in cardiac cells. Furthermore, it is known that a prolongation of the QTc-interval is indicative of and strongly correlated to a fatal form of cardiac arrhythmias (ventricular fibrillation) called torsades de pointes. It has now unexpectedly been found that the desethyl metabolite of oxybutynin and the optically active isomers thereof are free from said cardiac side effect of oxybutynin, while maintaining the therapeutic activities of oxybutynin or the optically active isomers thereof.

It has also been found that certain types of drugs that utilize the same or similar metabolic enzymes as oxybutynin, will further increase the risk for torsades des pointes when combined with oxybutynin. Examples of such drugs are ketoconazole and erythromycin.

This most unwanted side effect of oxybutynin is of concern in all patients given racemic oxybutynin and particularly in patients that are of age or patients that have pre-existing cardiovascular conditions for example long basal QTc interval.

It was found that both the R(−)-isomer and the S(+)-isomer of oxybutynin cause a prolongation of the QTc-interval of the EKG, while the corresponding isomers of DEO did not cause a prolongation of the QTc-interval. Since the duration of the QTc-interval is dose-dependently prolonged by these compounds, the risk for torsades des pointes arrhythmias is exceptionally high when S(+)-oxybutynin is given to the patients, since the S-isomer is administered in higher doses than the racemate. However, racemic oxybutynin is used at a dose of 5 mg several times daily for very long time periods and the risk for prolongation of QTc by such doses is very substantial. Examples of drugs that have been found to cause prolongation of QTc and consequently might cause torsades des pointes arrhythmias are terfenadine (Seldane®), astemizole (Hismanal®) and terodiline (Micturin®); all these drugs have been withdrawn from the market because of this side effect.

DETAILED DESCRIPTION OF THE INVENTION

CHEMISTRY

Racemic oxybutynin is 4-diethylamino-2-butynyl α-cyclohexyl-α-hydroxybenzeneacetate, also known as 4-diethylamino-2-butynyl cyclohexylphenylglycolate and herein also referred to as OXY. The generic name given to the hydrochloride salt of racemic oxybutynin by the USAN Council is oxybutvnin chloride; it is sold under the name of Ditropan®.

Racemic desethyloxybutynin is 4-ethylamino-2-butynyl cyclohexyl-phenylglycolate and is a known metabolite of oxybutynin (Hughes K. M. et al. Measurement of oxybutynin and its N-desethyl metabolite in plasma . . . Xenobiotica, 1992, 7: 859–869). This compound is herein referred to as DEO. No generic name is known for this compound or any of its salts.

The overall process for preparing DEO involves:
(a) the preparation of the side chain 4-ethylamino-2-butynyl chloride from dichlorobutyne
(b) by standard esterification technique, reacting cyclohexylphenyl glycolic acid with 4-ethylamino-2-butynyl chloride to produce 4-ethylamino-2-butynyl cyclohexylphenyl-glycolate (DEO).

An alternative process for preparing the compound of the invention involves the preparation of a hydroxylated side chain in stead of the above mentioned halogenated side chain.

Racemic cyclohexylphenylglycolic acid is commercially available from SIPSY Chem Corp., 2137 Route 33, Suite 2, Hamilton Square, N.J. 08690.

The process for preparing R-DEO is described in U.S. Pat. No. 6,123,961 and a process for preparing S-DEO is described in U.S. Pat. No. 5,532,278, the disclosures of which are hereby incorporated by reference.

DOSING, DOSAGE FORMS, PHARMACEUTICAL COMPOSITIONS

The magnitude of a prophylactic or therapeutic dose of the compound of this invention in the acute or chronic management of disease will vary with the severity and nature of the condition to be treated and the route of administration. The dose and the frequency of the dosing will also vary according to the age, body weight and response of the individual patient. In general, the total daily dose range for the compound of this invention for the conditions described herein is from about 1 mg to about 100 mg in single or divided doses, preferably in divided doses. In managing the patient, the therapy should be initiated at a lower dose, perhaps at about 0.5 mg to about 25 mg, and may be increased up to about 200 mg depending on the patient's global response. It is further recommended that patients over 65 years and those with impaired renal or hepatic function initially receive low doses and that they be titrated based on individual response(s) and plasma drug level(s). It may be necessary to use dosages outside these ranges, as will be apparent to those skilled in the art. Further, it is noted that the clinician or treating physician will know how and when to interrupt, adjust, or terminate therapy in conjunction with individual patient response. The terms "a therapeutically effective amount" and "an amount sufficient to treat urinary incontinence but insufficient to cause adverse effects" are encompassed by the above-described dosage amounts and dose frequency schedule.

Any suitable route of administration may be employed for providing the patient with an effective dosage of the compounds of this invention. For example, oral, sublingual, rectal, parental (subcutaneous, intramuscular, intravenous), intraocular, transdermal, aerosol and like forms of administration may be employed. Dosage forms include tablets, controlled-release tablets, troches, dispersions, suspensions, solutions, capsules, microencapsulated systems, sprays, transdermal delivery systems, and the like.

The pharmaceutical compositions of the present invention comprise a compound of the present invention as the active ingredient, or a pharmaceutically acceptable salt thereof, and may also contain a pharmaceutically acceptable carrier, and optionally, other therapeutic ingredients.

The terms "pharmaceutically acceptable salts" or "a pharmaceutically acceptable salt thereof" refer to salts prepared from pharmaceutically acceptable non-toxic acids. Suitable pharmaceutically acceptable acid addition salts for the compound of the present invention include acetic, benzenesulfonic (besylate), benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pathothenic, phosphoric, succinic, sulfuric, tartaric, p-toluenesulfonic, and the like. The hydrochloride is particularly preferred.

The compositions of the present invention include suspensions, solutions, elixirs or solid dosage forms. Carriers such as starches, sugars, and microcrystalline cellulose, diluents, granulating agents, lubricants, binders, disintegrating agents, and the like are suitable in the case of oral solid preparations (such as powders, capsules, and tablets), and oral solid preparations are preferred over the oral liquid preparations.

Because of their ease of administration, tablets and capsules represent one of the more advantageous oral dosage unit forms, in which case solid pharmaceutical carriers are employed. If desired, tablets may be coated by standard aqueous or nonaqueous techniques. Since the compound of the invention has a relatively short duration of action in the body, it may be advantageous to administer the drug in a controlled-released or slow-release formulation, thereby decreasing the frequency of drug administrations to the patient. The compounds of the present invention may also be administered by controlled release means and delivery devices such as those described in U.S. Pat. Nos.: 3,845,770; 3,916,899; 3,536,809; 3,598,123; and 4,008,719, and PCT application WO92/20377, the disclosures of which are hereby incorporated by reference. Various forms of controlled release or slow release transdermal administration forms and devices can also be used to improve the convenience of dosage for the patient and are hereby incorporated by reference.

Pharmaceutical compositions of the present invention suitable for oral administration may be presented as discrete unit dosage forms such as capsules, cachets, or tablets, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation, just as is known for the racemic mixture.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active agent or dispersing agent. Molded tablets may be made by molding, in a suitable machine, a mixture of the powdered compound moistened with an inert liquid diluent. All of the foregoing techniques are well know to persons of skill in the pharmaceutical art. Each tablet may contain from about 0.5 mg to about 25 mg of the active ingredient.

EXAMPLES

Example 1

ORAL UNIT DOSAGE FORMULATION
Tablets:

| Ingredients | per tablet | per batch of 10,000 tablets |
|---|---|---|
| Desethyloxybutynin | 5 mg | 50 g |
| Microcrystalline cellulose | 30 mg | 300 g |
| Lactose | 70 mg | 700 g |
| Calcium stearate | 2 mg | 20 g |
| FD&C Blue #1 Lake | 0.03 mg | 300 mg |

The selected compound of the present invention is blended with the lactose and cellulose until a uniform blend is formed. The lake is added and further blended. Finally, the calcium stearate is blended in, and the resulting mixture is compressed into tablets using a 9/32 inch (7 mm) shallow concave punch. Tablets of other strengths may be prepared by altering the ration of active ingredient to the excipients or to the final weight of the tablet.

The surprising utility of the compounds of the present invention have been established by the following studies.

Pharmacological Studies

MATERIALS AND METHODS

1. Ligand Binding Studies: Muscarinic Receptors.

The experiments are carried out on membranes prepared from SF9 cells infected with baculovirus to express human recombinant muscarinic receptor subtypes. After incubation with the test article and the proper radioligand and washing, bound radioactivity is determnined with a liquid scintillation counter, using a commercial scintillation cocktail. The specific radioligand binding to each receptor is defined as the difference between total binding and nonspecific binding determined in the presence of an excess of unlabelled ligand. $IC_{50}$ values (concentrations required to inhibit 50% of specific binding) are determined by non linear regression analysis of the competition curves. These parameters are obtained by curve fitting using Sigmaplot software.

2. Functional Characterization of Antimuscarinic/ Antispasmodic Activity.

Strips of intestinal smooth muscle tissue are removed from the body of male Hartley guinea pigs weighing 400–600 g. The strips are suspended in an oxygenated buffer of the following composition, in mM: NaCl, 133; KCl, 4.7; $CaCl_2$, 2.5; $MgSO_4$, 0.6; $NaH_2PO_4$, 1.3; $NaHCO_3$, 16.3; and glucose, 7.7, or a similar balanced physiological solution. They are maintained at constant temperature. Contractions are recorded with isometric transducers (Model FT-10) on an ink-writing polygraph.

In each experiment up to seven strips are removed from a single animal, suspended in individual tissue chambers and allowed to equilibrate with the bathing solution for one hour before proceeding with the experiment.

In order to assess the viability of each tissue and to serve as a frame of reference, contractions of each strip of tissue are recorded initially in response to exposure to a tissue medium in which the NaCl was replaced by KCl to yield a concentration of 137.7 mM KCl in the medium. This is followed by return to the standard medium, and then by exposures to progressively creasing concentrations of carbachol, with separate exposures to each concentration only until the peak response has been recorded. Then, leaving one strip untreated and/or one strip exposed to the test solution to serve as control tissue(s), the remaining strips each are exposed for one hour to one concentration of an antagonist. Finally, the responses to increasing concentrations of carbachol followed by exposure to 137.7 mM KCl are recorded a second time. To determine whether antagonists decrease the peak response to agonists, the peak tension developed by each strip during the second set of determinations is expressed as a percent of the peak tension developed during the first concentration-effect determination. Then, for each antagonist the resultant data are analyzed using standard statistical methodology.

3. Cardiac side effects.

Male guinea pigs (450–600 g) are anesthetized with freshly prepared dialurethane sodium. The jugular vein is catheterized for iv administration of test drugs and the trachea is exposed and cannulated. Subdermal electrodes are positioned for Lead II electrocardiogram recording, monitored on a Grass Polygraph recorder, set at a paper speed of 50 nmmsec. The animals are allowed to stabilize for 30 minute after completion of surgery, and three baseline EKG recordings are then made at 10-minute intervals. The animals are then given a dose of the test compound or vehicle as an intravenous inflision over 30 min. EKG recordings are used to determine QT intervals and heart rates. To compensate for variations in heart rates, QTc intervals are calculated from QT- and RR-intervals as known to those skilled in the art. Prolongation of QTc is indicative of a prolonged action potential, caused by an inhibition of the delayed rectifier potassium channel. Prolongation of QTc is the known cause of Torsades de Pointes ventricular fibrillation by drugs such as terfenadine and astemizole (now withdrawn from the market).

EQUIVALENTS

Those skilled in the art will recognize, or be able to ascertain, using no more than routine experimentation, many equivalents to the specific embodiments of the invention described herein. Such equivalents include salt forms e.g. sulfate, fumarate, hydrobromide, hydrochloride, dihydrochloride, methanesulphonate, hydroxynaphthoate, chlorotheophylline or where appropriate one or other of the hydrate forms thereof, see Merck Index 11th edition (1989) items 9089, 209, 3927, 4628, 8223, 5053, 5836, 8142, 2347, 7765, 1840, 9720, 7461, 1317, 4159, and 963 and references cited therein and Am. Rev. Resp. Dis. 1988, 137: (4;2/2) 32. Such equivalents also include the co-administration of at least one compound of the present invention with any other drug that is used to combat diseases in mammals, mentioned in this document. Such equivalents also include the co-administration of at least one compound of the present invention with any other compound or drug that may be used in combination with medication for urinary incontinence or intestinal hyperactivity. Those skilled in the art of medicine will also realize that higher or lower doses than those indicated here may be preferred and the doses may be given more or less frequently than suggested here.

The optically active isomers of the des-ethyl metabolite of oxybutynin do not cause a prolongation of the QTc interval of the ECG are therefore not arrhythmogenic and are intended to be included in this present invention. The R-isomer of the des-ethyl metabolite of oxybutynin is a potent antimuscarinic agent and is useful in patients suffering from cholinergic and other forms of urinary incontinence and other smooth muscle spasms, including intestinal hypermotility disorders. The S-isomer of the des-ethyl metabolite of oxybutynin is a spasmolytic agent with weak anticholinergic activity and is useful in patients suffering from various forms of urinary incontinence and smooth muscle spasms, including intestinal hypermotility disorders. The pharmaceutically acceptable salts of the isomers of the des-ethyl metabolite of oxybutynin are also intended to be included in this present invention.

The didesethyl metabolite of oxybutynin has pharmacological activities that are similar to those of des-ethyl oxybutynin, although the didesethyl metabolite has somewhat lower affinity for muscarinic and the benzothiazepine receptors than the des-ethyl metabolite. Since the didesethyl metabolite does not prolong the QTc interval of the ECG, this metabolite and its optically active isomers and the salt forms thereof are intended to be included into the present invention.

Those skilled in the art, will realize that the terms intestinal hyperactivity disorders and intestinal hypermotility disorders include irritable bowel syndromes (IBS).

Those skilled in the art of pharmacology, will realize that the compounds of the invention, having certain pharmacological properties (such as antimuscarinic activity on various receptor types, calcium antagonistic activity, spasmolytic activity on various types of smooth muscle etc.) may be useful for other indications than those listed here. Such indications are equivalents to the specific embodiments of the invention described herein.

All equivalents are intended to be included in this present invention.

What is claimed is:

1. A method for treating disorders involving the urethrogenital tract, which method comprises administering to a mammal in need of such treatment a therapeutically effective amount of racemic 4-ethylamino-2-butynyl cyclohexyl-phenylglycolate or a pharmaceutically acceptable salt thereof while avoiding the adverse side effect of QTc prolongation associated with 4-diethylamino-2-butynyl cyclohexylphenylglycolate.

2. The method of claim 1, wherein said disorder involving the urethrogenital tract is urinary incontinence.

3. The method of claim 1, wherein said racemic 4-ethylamino-2-butynyl cyclohexyl-phenylglycolate or a pharmaceutically acceptable salt thereof, is administered while avoiding the side effects of racemic 4-diethylamino-2-butynyl cyclohexyl-phenylglycolate.

4. The method of claim 3, wherein said side effect is cardiac arrhythmia.

5. The method of claim 1, wherein said racemic 4-ethylamino-2-butynyl cyclohexylphenylglycolate, or a pharmaceutically acceptable salt thereof, is administered by inhalation or by parenteral, transdermal, rectal, sublingual or oral administration.

6. The method of claim 1, wherein said racemic 4-ethylamino-2-butynyl cyclohexylphenylglycolate, or a pharmaceutically acceptable salt thereof, is administered by oral administration as an extended release or controlled release formulation.

7. The method of claim 1, wherein said racemic 4-ethylamino-2-butynyl cyclohexylphenylglycolate, or a pharmaceutically acceptable salt thereof, is administered in a dose of from about 0.5 mg to about 200 mg per day.

* * * * *